US012365848B2

(12) United States Patent
Yin et al.

(10) Patent No.: US 12,365,848 B2
(45) Date of Patent: Jul. 22, 2025

(54) METHOD FOR PREPARING HIGH VISCOSITY INDEX POLY-ALPHA-OLEFIN

(71) Applicants: CHINA PETROLEUM & CHEMICAL CORPORATION, Beijing (CN); SHANGHAI RESEARCH INSTITUTE OF CHEMICAL INDUSTRY CO., LTD., Shanghai (CN)

(72) Inventors: Zhaolin Yin, Guangdong (CN); Yucai Cao, Shanghai (CN); Dongwen Zhong, Guangdong (CN); Shengbiao Liang, Guangdong (CN); Yongqing Li, Shanghai (CN); Zhenyu Liu, Guangdong (CN); Lujian Li, Guangdong (CN); Xiaofeng Ye, Shanghai (CN); Weizhe Wang, Guangdong (CN); Chen Ni, Shanghai (CN); Jie Li, Guangdong (CN); Fan Wang, Shanghai (CN); Guoyu Liu, Guangdong (CN); Shibing Chen, Guangdong (CN); Xionghua Chen, Guangdong (CN); Wenjun Jiang, Guangdong (CN); Zhenxu Lu, Guangdong (CN); Si Tan, Guangdong (CN); Ruizhen Lu, Guangdong (CN)

(73) Assignees: CHINA PETROLEUM & CHEMICAL CORPORATION, Beijing (CN); SHANGHAI RESEARCH INSTITUTE OF CHEMICAL INDUSTRY CO., LTD., Shanghai (CN)

( * ) Notice: Subject to any disclaimer, the term of this patent is extended or adjusted under 35 U.S.C. 154(b) by 0 days.

(21) Appl. No.: 17/755,536

(22) PCT Filed: Oct. 30, 2020

(86) PCT No.: PCT/CN2020/125118
§ 371 (c)(1),
(2) Date: Apr. 30, 2022

(87) PCT Pub. No.: WO2021/083307
PCT Pub. Date: May 6, 2021

(65) Prior Publication Data
US 2022/0403278 A1 Dec. 22, 2022

(30) Foreign Application Priority Data

Oct. 30, 2019 (CN) .......................... 201911046738.0

(51) Int. Cl.
C10M 107/10 (2006.01)
C08F 4/6592 (2006.01)
C08F 10/14 (2006.01)
C10N 20/02 (2006.01)
C10N 20/04 (2006.01)
C10N 30/02 (2006.01)

(52) U.S. Cl.
CPC ....... C10M 107/10 (2013.01); C08F 4/65927 (2013.01); C08F 10/14 (2013.01); *C10M 2205/0285* (2013.01); *C10N 2020/02* (2013.01); *C10N 2020/04* (2013.01); *C10N 2030/02* (2013.01)

(58) Field of Classification Search
CPC ......... C10M 107/10; C10M 2205/0285; C08F 4/65927; C08F 10/14; C10N 2020/02; C10N 2020/04; C10N 2030/02
See application file for complete search history.

(56) References Cited

U.S. PATENT DOCUMENTS

| 4,072,809 A | 2/1978 | Rogan | |
|---|---|---|---|
| 7,666,957 B2 | 2/2010 | Kallio et al. | |
| 2007/0000807 A1* | 1/2007 | Wu | C10M 169/04 208/18 |
| 2007/0298990 A1* | 12/2007 | Carey | C10M 111/04 508/591 |
| 2009/0036725 A1* | 2/2009 | Wu | C08F 10/00 585/521 |
| 2009/0281360 A1* | 11/2009 | Knowles | B01J 8/20 585/12 |
| 2010/0087349 A1* | 4/2010 | Lee | C10M 111/04 508/499 |
| 2010/0317904 A1* | 12/2010 | Small | C07C 5/05 585/524 |
| 2014/0039137 A1* | 2/2014 | Giesbrecht | C08F 4/76 526/133 |
| 2014/0135461 A1* | 5/2014 | Kohiruimaki | C08F 6/008 526/170 |
| 2014/0213834 A1* | 7/2014 | Patil | C10M 107/10 585/509 |

(Continued)

FOREIGN PATENT DOCUMENTS

| CN | 101130467 A | 2/2008 |
|---|---|---|
| CN | 102803312 A | 11/2012 |

(Continued)

*Primary Examiner* — Ellen M McAvoy
(74) *Attorney, Agent, or Firm* — NKL Law; Allen Xue

(57) ABSTRACT

A method for preparing a high viscosity index poly-α-olefin subjects α-olefin to a polymerization reaction in the presence of a metallocene catalyst to obtain a poly-α-olefin. The polymerization reaction is carried out in the absence of a solvent, and the metallocene catalyst is formed of, or is formed by interaction between, a metallocene compound and an activator.

17 Claims, No Drawings

(56) References Cited

U.S. PATENT DOCUMENTS

| | | | |
|---|---|---|---|
| 2014/0275664 A1* | 9/2014 | Yang | B01J 31/143 585/18 |
| 2015/0158958 A1* | 6/2015 | Harrington | C08F 4/64189 526/144 |
| 2016/0264493 A1 | 9/2016 | Small et al. | |
| 2017/0114166 A1* | 4/2017 | Harada | C08F 210/16 |
| 2017/0226441 A1* | 8/2017 | Courtiade | C10M 107/10 |
| 2018/0237554 A1* | 8/2018 | Holtcamp | C08F 4/65927 |
| 2018/0282443 A1* | 10/2018 | Crowther | C08F 10/14 |
| 2023/0002514 A1* | 1/2023 | Harlan | C08F 4/025 |

FOREIGN PATENT DOCUMENTS

| | | |
|---|---|---|
| CN | 103304717 A | 9/2013 |
| CN | 104926963 A | 9/2015 |
| CN | 106380529 A | 2/2017 |
| IN | 103562238 A | 2/2014 |
| JP | 2000034313 A | 2/2000 |
| JP | 2002121202 A | 4/2002 |
| JP | 2006206925 A | 8/2006 |
| JP | 2010534762 A | 11/2010 |
| JP | 2012092199 A | 5/2012 |
| JP | 2012515821 A | 7/2012 |
| JP | 2013537576 A | 10/2013 |
| WO | 2013161833 A1 | 10/2013 |
| WO | 2018185173 A1 | 10/2018 |
| WO | 2018193894 A1 | 10/2018 |

* cited by examiner

METHOD FOR PREPARING HIGH VISCOSITY INDEX POLY-ALPHA-OLEFIN

CROSS-REFERENCE TO RELATED APPLICATIONS

This application is a U.S. national stage entry of PCT international application no. PCT/CN2020/125118, filed Oct. 30, 2020, which claims to the priority of the Chinese patent application titled "Method for preparing high viscosity index poly-alpha-olefin" with the application number of CN201911046738.0 filed on Oct. 30, 2019, the entirety of which is incorporated herein by reference.

FIELD OF THE INVENTION

The present invention relates to a method for preparing a poly-alpha-olefin with a high viscosity index, and in particular to a method for preparing a poly-alpha-olefin with a high viscosity index in the presence of a metallocene catalyst and use of the prepared poly-alpha-olefin with a high viscosity index in a lubricating oil. The invention is applied in the technical field of a lubricating oil.

BACKGROUND OF THE INVENTION

A lubricating oil is a liquid lubricant used in various types of machinery to reduce friction and protect machinery and processed parts, and mainly plays a role in lubrication, cooling, rust prevention, cleaning, sealing, buffering, etc. The use of advanced lubricating materials and new lubricating and sealing technologies can enable mechanical equipment to work lastingly and stably under more severe operating conditions (such as high temperature, high speed, heavy load, special medium environment, etc.), improve mechanical efficiency, reduce maintenance and shutdown losses, save energy and reduce material consumption, and improve comprehensive economic benefits. A Poly-Alpha-Olefin (or Poly-Alpha-Olefins, PAO for short) is a synthetic hydrocarbon lubricating oil prepared by a chemical synthesis method, and is currently considered to be the most promising synthetic lubricating oil.

The PAO is usually obtained by a polymerization reaction catalyzed with a traditional catalyst such as Lewis acid, Zieger-Natta catalyst, etc. For example, catalyzation is performed with a $BF_3$ catalyst to prepare a low-viscosity PAO. Catalyzation is performed with a $AlCl_3$ catalyst to prepare a medium-viscosity PAO. Catalyzation is performed with a Zieger-Natta catalyst to prepare a high-viscosity PAO. The PAO prepared by these methods usually possess a protruding backbone from which short or long side chains protrude in a disordered manner.

A metallocene poly-alpha-olefin is obtained by catalyzing the polymerization of an α-olefin with a metallocene catalyst, and due to its unique geometric structure, a very uniform product can be obtained. Thus, the metallocene PAO product has a comb-like structure without vertical side chains. This structure further affects properties of the PAO product. Compared with a traditional PAO, the metallocene PAO (mPAO) usually possesses improved rheological characteristics and flow features, thereby providing better shear stability, a lower pour point and a higher viscosity index, and possessing good viscosity-temperature characteristics. These characteristics determine that the mPAO can be used in the highly severe environment, including power transmission system and gear oils, compressor lubricant oils, transmission fluids and industrial lubricant oils.

Currently, most of the methods for preparing the mPAO have a complex catalytic system, and require the use of a large number of organic solvents to cause separation, energy consumption and environmental protection problems. Moreover, the prepared products have a low viscosity index, and are limited to be used in extreme conditions. All these factors hinder their large-scale industrial production application.

SUMMARY OF THE INVENTION

The first technical problem to be solved by the invention is that in the prior art, the catalyst (e.g., a metallocene catalyst) usually needs to be dissolved in a solvent to obtain a homogeneous system, but the solvent introduced in this process needs an additional step for removal. The invention provides a new method for preparing a poly-alpha-olefin with a high viscosity index. By using a specific activator in coordination with a specific metallocene compound, the metallocene catalyst containing these two substances and an α-olefin raw material can form a homogeneous system, thereby avoiding the use of the solvent and the subsequent step of removing the solvent. Furthermore, it is unexpectedly found that the poly-alpha-olefin obtained by the method of the invention has a higher viscosity index.

The second technical problem to be solved by the invention is to provide a poly-alpha-olefin prepared by the method for solving the first technical problem.

The third technical problem to be solved by the invention is use of the poly-alpha-olefin prepared by the method of the above first technical problem or the poly-alpha-olefin of the above second technical problem in a lubricating oil.

The fourth technical problem to be solved by the invention is a lubricating oil comprising the poly-alpha-olefin prepared by the method of the above first technical problem or the poly-alpha-olefin of the above second technical problem.

In order to solve the above first technical problem, the technical solution adopted by the invention is indicated as follows:

a method for preparing a poly-alpha-olefin with a high viscosity index, comprising subjecting an α-olefin to a polymerization reaction in the presence of a metallocene catalyst to obtain a poly-alpha-olefin, wherein the polymerization reaction is carried out in the absence of a solvent, the metallocene catalyst is formed of, or is formed by interaction between, a metallocene compound and an activator, wherein the metallocene compound has a structure as represented by formula (I):

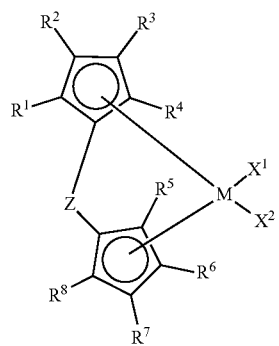

Formula (I)

in the formula (I), M is a Group IV metal, preferably titanium, zirconium or hafnium, $X^1$ and $X^2$ are each independently selected from a group consisting of halogen, $C_1$-$C_{10}$ alkyl, $C_6$-$C_{10}$ aryl, $C_1$-$C_{10}$ substituted alkyl, and $C_6$-$C_{10}$ substituted aryl, and optionally, one or more carbons in the alkyl or aryl are substituted by heteroatoms, $R^1$, $R^2$, $R^3$, $R^4$, $R^5$, $R^6$, $R^7$ and $R^8$ are each independently selected from a group consisting of H, $C_1$-$C_{20}$ alkyl, $C_6$-$C_{20}$ aryl, $C_1$-$C_{20}$ substituted alkyl and $C_6$-$C_{20}$ substituted aryl, and optionally, one or more carbons in the alkyl or aryl are substituted by heteroatoms, adjacent groups in $R^1$, $R^2$, $R^3$, $R^4$, $R^5$, $R^6$, $R^7$ and $R^8$ are optionally bonded to each other to form cyclopentadienyl-aryl with a five-membered ring to which they are connected, Z is silicon or carbon that achieves valence saturation through a substituent, and the substituent is any one of $C_1$-$C_{20}$ alkyl, $C_1$-$C_{20}$ substituted alkyl and $C_6$-$C_{20}$ aryl, and the activator includes an alkylaluminium and/or a borate, preferably including an alkylaluminium and a borate.

According to a preferred embodiment of the invention, the molar ratio of the alkylaluminium to the borate is (0.0001~5000):1, preferably (0.001~500):1, more preferably (0.005~50):1, and further preferably (0.01~20):1.

According to the invention, when the molar ratio of the alkylaluminium to the borate falls within the above ranges, it is favorable to enable the metallocene catalyst to form a homogeneous system in the α-olefin, thereby facilitating carrying out the polymerization reaction.

According to a preferred embodiment of the invention, the molar ratio of the alkylaluminium to the borate may be 0.0001:1, 0.001:1, 0.005:1, 0.01:1, 0.05:1, 0.1:1, 0.5:1, 1:1, 5:1, 10:1, 15:1, 20:1, 25:1, 30:1, 35:1, 40:1, 45:1, 50:1, 55:1, 50:1, 65:1, 70:1, 75:1, 80:1, 85:1, 90:1, 95:1, 100:1, 200:1, 300:1, 400:1, 500:1, 600:1, 700:1, 800:1, 900:1, 1000:1 and any value between them.

According to a preferred embodiment of the invention, the alkylaluminium has a general formula of $AlR_3$, wherein R is $C_1$-$C_{10}$ alkyl. Preferably, the alkylaluminium is selected from a group consisting of trimethylaluminum, triethylaluminum, triisopropylaluminum, tri-n-propylaluminum, triisobutylaluminum, tri-n-butylaluminum, triisoamylaluminum, tri-n-pentylaluminum, triisohexylaluminum, tri-n-hexylaluminum, triisoheptylaluminum, tri-n-heptylaluminum, triisooctylaluminum, tri-n-octylaluminum, triisononylaluminum, tri-n-nonylaluminum, triisodecylaluminum, and tri-n-decylaluminum.

According to a preferred embodiment of the invention, the borate is selected from a group consisting of dimethylanilinium tetrakis(pentafluorophenyl)borate, diethylanilinium tetrakis(pentafluorophenyl)borate, dibutylanilinium tetrakis(pentafluorophenyl)borate, trimethylammonium tetrakis(pentafluorophenyl)borate, diethylammonium tetrakis(pentafluorophenyl)borate and tributylammonium tetrakis(pentafluorophenyl)borate.

According to a preferred embodiment of the invention, the α-olefin is a $C_4$-$C_{20}$ α-olefin, preferably a $C_6$-$C_{14}$ α-olefin, more preferably 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadene and 1-eicosene, or preferably 1-butene, 1-pentene, 1-hexene, 1-heptene, 1-octene, 1-nonene, 1-decene, 1-undecene, 1-dodecene, 1-tridecene and 1-tetradecene.

According to a preferred embodiment of the invention, the conditions for the polymerization reaction include: a reaction temperature of 20° C. to 200° C., preferably 60° C. to 170° C.

According to a preferred embodiment of the invention, by calculating the alkylaluminium with Al and the metallocene compound with M, the molar ratio of the alkylaluminium to the metallocene compound is 0.1:1~1000:1, preferably 0.1:1~100:1.

According to a preferred embodiment of the invention, by calculating the alkylaluminium with Al and the metallocene compound with M, the molar ratio of the alkylaluminium to the metallocene compound may be 0.1:1, 1:1, 5:1, 10:1, 15:1, 20:1, 25:1, 30:1, 35:1, 40:1, 45:1, 50:1, 55:1, 50:1, 65:1, 70:1, 75:1, 80:1, 85:1, 90:1, 95:1, 100:1, 200:1, 300:1, 400:1, 500:1, 600:1, 700:1, 800:1, 900:1, 1000:1 and any value between them.

According to a preferred embodiment of the invention, by calculating the borate with B and the metallocene compound with M, the molar ratio of the borate to the metallocene compound is 0.1:1~1000:1, preferably 0.1:1~100:1.

According to a preferred embodiment of the invention, by calculating the borate with B and the metallocene compound with M, the molar ratio of the borate to the metallocene compound may be 0.1:1, 1:1, 5:1, 10:1, 15:1, 20:1, 25:1, 30:1, 35:1, 40:1, 45:1, 50:1, 55:1, 50:1, 65:1, 70:1, 75:1, 80:1, 85:1, 90:1, 95:1, 100:1, 200:1, 300:1, 400:1, 500:1, 600:1, 700:1, 800:1, 900:1, 1000:1 and any value between them.

According to a preferred embodiment of the invention, the mass ratio of the metallocene compound to the α-olefin is $(10^{-6}\text{-}10^{-3})$:1, preferably $(10^{-5}\text{-}10^{-4})$:1.

According to a preferred embodiment of the invention, the mass ratio of the metallocene compound to the α-olefin may be $10^{-6}$:1, $5 \times 10^{-6}$:1, $10^{-5}$:1, $5 \times 10^{-5}$:1, $10^{-4}$:1, $5 \times 10^{-4}$:1, $10^{-3}$:1 and any value between them.

According to a preferred embodiment of the invention, in the formula (I), M is zirconium.

According to a preferred embodiment of the invention, in the formula (I), $X^1$ and $X^2$ are each independently selected from a group consisting of chlorine, $C_1$-$C_4$ alkyl or $C_1$-$C_4$ substituted alkyl, and optionally, one or more carbons in the alkyl are substituted by heteroatoms.

According to a preferred embodiment of the invention, in the formula (I), $X^1$ and $X^2$ are chlorine.

According to a preferred embodiment of the invention, in the formula (I), $R^1$, $R^2$, $R^3$, $R^4$, $R^5$, $R^6$, $R^7$ and $R^8$ are each independently selected from a group consisting of H, $C_1$-$C_{10}$ alkyl, $C_6$-$C_{15}$ aryl, $C_1$-$C_{10}$ substituted alkyl, and $C_6$-$C_{15}$ substituted aryl. Preferably, $R^1$, $R^2$, $R^3$, $R^4$, $R^5$, $R^6$, $R^7$ and $R^8$ are each independently selected from a group consisting of H, $C_1$-$C_6$ alkyl, $C_6$-$C_{12}$ aryl, $C_1$-$C_6$ substituted alkyl, and $C_6$-$C_{10}$ substituted aryl, and optionally, one or more carbons in the alkyl or aryl are substituted by heteroatoms.

According to a preferred embodiment of the invention, in the formula (I), $R^1$, $R^2$, $R^3$, $R^4$, $R^5$, $R^6$, $R^7$ and $R^8$ are each independently selected from a group consisting of H, methyl, ethyl, propyl, isopropyl, butyl, isobutyl, phenyl and naphthyl.

According to a preferred embodiment of the invention, in the formula (I), Z is silicon that achieves valence saturation through a substituent. Preferably, the substituent is any one of $C_1$-$C_{10}$ alkyl, $C_1$-$C_{10}$ substituted alkyl and $C_6$-$C_{18}$ aryl, preferably any one of $C_1$-$C_6$ alkyl, $C_1$-$C_6$ substituted alkyl and $C_6$-$C_{12}$ aryl.

According to a preferred embodiment of the invention, the metallocene compound is selected from the following compounds:
dimethylsilylbis-n-propylcyclopentadienylzirconium dichloride;
dimethylsilylbisindenylzirconium dichloride;
diethylsilylbisindenylzirconium dichloride;
diphenylsilylbis(4,7-dimethylindenyl)zirconium dichloride;
dimethylsilylbis(4,7-dimethylindenyl)zirconium dichloride;
dimethylsilylbisindenylzirconium dichloride;
diphenylsilylbis(2-methylcyclopentadienyl)zirconium dichloride;
ethylenebisindenylzirconium dichloride;
ethylenebis(2-methylindenyl)zirconium dichloride;
dimethylsilylbis(2-methyl-3-butylcyclopentadienyl)zirconium dichloride;
dimethylsilylbiscyclopentadienylzirconium dichloride;
diethylmethylenecyclopentadienyl(3,5-dimethylphenylindenyl)zirconium dichloride;
diethylmethylenecyclopentadienyl(4,7-dimethylindenyl)zirconium dichloride;
dimethylmethylenecyclopentadienyl(4,7-dimethylindenyl) zirconium dichloride;
dimethylsilylcyclopentadienyl(4,7-dimethylindenyl)zirconium dichloride;
dimethylsilylcyclopentadienyl(3,5-dimethylphenylindenyl) zirconium dichloride;
dimethylsilylbis(2-methylcyclopentadienyl)zirconium dichloride;
dimethylsilylbis(2-methylindenyl)zirconium dichloride;
dimethylsilylcyclopentadienyl(2-methylindenyl)zirconium dichloride;
dimethylsilylbis-n-propylcyclopentadienyl hafnium dichloride;
dimethylsilylbis-indenyl hafnium dichloride;
diethylsilylbis-indenyl hafnium dichloride;
diphenylsilylbis(4,7-dimethylindenyl)hafnium dichloride;
dimethylsilylbis(4,7-dimethylindenyl)hafnium dichloride;
dimethylsilylbis-indenyl hafnium dichloride;
diphenylsilylbis(2-methylcyclopentadienyl)hafnium dichloride;
ethylenebisindenylhafnium dichloride;
ethylenebis(2-methylindenyl)hafnium dichloride;
dimethylsilylbis(2-methyl-3-butylcyclopentadienyl)hafnium dichloride;
dimethylsilylbiscyclopentadienyl hafnium dichloride;
diethylmethylenecyclopentadienyl(3,5-dimethylphenylindenyl)hafnium dichloride;
diethylmethylenecyclopentadienyl(4,7-dimethylindenyl) hafnium dichloride;
dimethylmethylenecyclopentadienyl(4,7-dimethylindenyl) hafnium dichloride;
dimethylsilylcyclopentadienyl(4,7-dimethylindenyl)hafnium dichloride;
dimethylsilylcyclopentadienyl(3,5-dimethylphenylindenyl) hafnium dichloride;
dimethylsilylbis(2-methylcyclopentadienyl)hafnium dichloride;
dimethylsilylbis(2-methylindenyl)hafnium dichloride; and
dimethylsilylcyclopentadienyl(2-methylindenyl)hafnium dichloride.

According to a preferred embodiment of the invention, by the above preparation method, the poly-alpha-olefin with a high viscosity index can be obtained without adding additional hydrogen. However, if additional hydrogen is added, the conversion rate of the α-olefin can be further improved, and/or the molecular weight of the poly-alpha-olefin can be reduced, and/or the activity of the poly-alpha-olefin can be improved.

In order to solve the above second technical problem, the technical solution adopted by the invention is indicated as follows:
a poly-alpha-olefin prepared by the above method.

According to a preferred embodiment of the invention, after the polymerization reaction is completed, unreacted monomers and oligomerization products are removed by separation to obtain the poly-alpha-olefin.

According to a preferred embodiment of the invention, the poly-alpha-olefin has a viscosity index of above 140, preferably above 180, and more preferably above 200.

According to a preferred embodiment of the invention, the poly-alpha-olefin has 100° C. kinematic viscosity of above 3 cSt, preferably above 50 cSt, and more preferably above 100 cSt.

According to a preferred embodiment of the invention, the poly-alpha-olefin has a weight average molecular weight of 200~50,000.

In order to solve the above third technical problem, the technical solution adopted by the invention is indicated as follows:
use of the poly-alpha-olefin prepared by the above method or the above poly-alpha-olefin in a lubricating oil.

According to a preferred embodiment of the invention, the poly-alpha-olefin is directly applied to the lubricating oil without performing a further separation or blending operation. Preferably, the separation comprises separating impurities from the poly-alpha-olefin, and the impurities include a solvent.

According to the invention, the poly-alpha-olefin prepared by the above method or the above poly-alpha-olefin is particularly suitable for use in a lubricating oil for the following reasons:
1) the poly-alpha-olefin prepared by the above method or the above poly-alpha-olefin has a higher viscosity index which is usually above 140; and
2) the poly-alpha-olefin prepared by the above method or the above poly-alpha-olefin may be directly applied to the lubricating oil without performing further separation or blending, which can simplify the production process and has a broad industrial application prospect.

In order to solve the above fourth technical problem, the technical solution adopted by the invention is indicated as follows:
a lubricating oil comprising the poly-alpha-olefin prepared by the above method or the above poly-alpha-olefin, and optionally a lubricating oil additive.

According to the invention, the lubricating oil additive may be one or several compounds commonly used to be added to the lubricating oil in the art so as to enable the lubricating oil to obtain certain new characteristics or improve some existing characteristics of the lubricating oil. The lubricating oil additive is selected from a group consisting of an antioxidant, an antiwear agent, a friction modifier (also known as an oiliness agent), an extreme pressure additive, a detergent, a dispersant, a foam inhibitor, a corrosion and rust inhibitor, a flow point improver and a viscosity index enhancer.

According to the invention, the specific type of the lubricating oil additive may be conventionally selected according to different requirements brought about by different occasions to which the lubricating oil is applied.

According to the invention, the content of the lubricating oil additive may be conventionally selected according to different requirements brought about by different occasions to which the lubricating oil is applied.

According to the invention, a method for preparing a lubricating oil using the poly-alpha-olefin and the lubricating oil additive is a conventional technical means in the art, and will not be repeated here.

In the invention, the term "high viscosity index" means that the viscosity index is above 140.

In the invention, the term "heteroatoms" may refer to heteroatoms such as oxygen, sulfur, nitrogen, phosphorus, etc.

In the invention, the term substituted alkyl or substituted aryl means that one or more hydrogen in the alkyl or aryl is substituted by a substituent. The substituent may be selected from a group consisting of halogen, a non-carbon oxyacid group and derivatives thereof, and optionally substituted alkyl, aralkyl and aryl, for example a group substituted by a group selected from a group consisting of alkyl, aryl, amino, hydroxyl, alkoxy, carbonyl, oxa, carboxyl, thia, sulfur oxyacid, a halogen and combinations thereof.

The beneficial effects of the invention at least lie in that the method for preparing a poly-alpha-olefin with a high-viscosity index provided by the invention is performed in the absence of a solvent, and the poly-alpha-olefin with a high viscosity index can be obtained without adding additional hydrogen, which is economical and environmentally friendly with strong operability and suitability for industrial production.

DETAILED DESCRIPTION OF THE EMBODIMENTS

The invention will be further described below through examples.

In the invention, the 100° C. kinematic viscosity is measured with reference to a test method of GB/T 265, and the viscosity index is calculated with reference to a calculation method of GB/T 1995.

Example 1

100 g of 1-hexene was added to a 250 mL flask filled with nitrogen. Heating was performed constantly at 120° C. for 30 minutes. 32 mg of dimethylanilinium tetrakis(pentafluorophenyl)borate, 40 mg of trimethylaluminum and 2 µmol of dimethylsilylbis-n-propylcyclopentadienylzirconium dichloride were added successively. After the reaction was performed for 1 h, a small amount of isopropanol was added to terminate the reaction. After the temperature dropped to room temperature, the mixture was filtered and distilled under reduced pressure to obtain 70.52 g of a product with a yield of 70%. The 100° C. kinematic viscosity was 120.6 cSt. The viscosity index was 237. The weight average molecular weight was 6,102.

Example 2

100 g of 1-hexene was added to a 250 mL flask filled with nitrogen. Heating was performed constantly at 80° C. for 30 minutes. 32 mg of dimethylanilinium tetrakis(pentafluorophenyl)borate, 40 mg of trimethylaluminum and 3 µmol of dimethylsilylbis-n-propylcyclopentadienylhafnium dichloride were added successively. After the reaction was performed for 1 h, a small amount of isopropanol was added to terminate the reaction. After the temperature dropped to room temperature, the mixture was filtered and distilled under reduced pressure to obtain 75.38 g of a product with a yield of 75%. The 100° C. kinematic viscosity was 111.8 cSt. The viscosity index was 220. The weight average molecular weight was 5,797.

Example 3

100 g of 1-octene was added to a 250 mL flask filled with nitrogen. Heating was performed constantly at 120° C. for 30 minutes. 32 mg of dimethylanilinium tetrakis(pentafluorophenyl)borate, 40 mg of trimethylaluminum and 3 µmol of dimethylsilylbis-n-propylcyclopentadienylzirconium dichloride were added successively. After the reaction was performed for 1 h, a small amount of isopropanol was added to terminate the reaction. After the temperature dropped to room temperature, the mixture was filtered and distilled under reduced pressure to obtain 95.25 g of a product with a yield of 95%. The 100° C. kinematic viscosity was 108.9 cSt. The viscosity index was 238. The weight average molecular weight was 5,696.

Example 4

100 g of 1-octene was added to a 250 mL flask filled with nitrogen. Heating was performed constantly at 100° C. for 30 minutes. 32 mg of dimethylanilinium tetrakis(pentafluorophenyl)borate, 40 mg of trimethylaluminum and 3 µmol of dimethylsilylbis-n-propylcyclopentadienylhafnium dichloride were added successively. After the reaction was performed for 1 h, a small amount of isopropanol was added to terminate the reaction. After the temperature dropped to room temperature, the mixture was filtered and distilled under reduced pressure to obtain 96.72 g of a product with a yield of 96%. The 100° C. kinematic viscosity was 100.2 cSt. The viscosity index was 230. The weight average molecular weight was 5,394.

Example 5

100 g of 1-octene was added to a 250 mL flask filled with nitrogen. Heating was performed constantly at 105° C. for 30 minutes. 32 mg of dimethylanilinium tetrakis(pentafluorophenyl)borate, 55 mg of triethylaluminium and 3 µmol of dimethylsilylbis-n-propylcyclopentadienylzirconium dichloride were added successively. After the reaction was performed for 1 h, a small amount of isopropanol was added to terminate the reaction. After the temperature dropped to room temperature, the mixture was filtered and distilled under reduced pressure to obtain 94.56 g of a product with a yield of 94%. The 100° C. kinematic viscosity was 101.7 cSt. The viscosity index was 229. The weight average molecular weight was 5,446.

Example 6

100 g of 1-octene was added to a 250 mL flask filled with nitrogen. Heating was performed constantly at 120° C. for 30 minutes. 55 mg of dibutylanilinium tetrakis(pentafluorophenyl)borate, 40 mg of trimethylaluminum, 71 mg of triisopropylaluminum and 3 µmol of dimethylsilylbis-n-propylcyclopentadienylzirconium dichloride were added successively. After the reaction was performed for 1 h, a small amount of isopropanol was added to terminate the reaction. After the temperature dropped to room temperature, the mixture was filtered and distilled under reduced pressure to obtain 92.63 g of a product with a yield of 92%.

The 100° C. kinematic viscosity was 23.2 cSt. The viscosity index was 203. The weight average molecular weight was 2,721.

Example 7

100 g of 1-octene was added to a 250 mL flask filled with nitrogen. Heating was performed constantly at 120° C. for 30 minutes. 35 mg of trimethylammonium tetrakis(pentafluorophenyl)borate, 102 mg of tri-n-propylaluminum and 2 μmol of dimethylsilylbisindenylzirconium dichloride were added successively. After the reaction was performed for 2 h, a small amount of isopropanol was added to terminate the reaction. After the temperature dropped to room temperature, the mixture was filtered and distilled under reduced pressure to obtain 81.72 g of a product with a yield of 81%. The 100° C. kinematic viscosity was 5 cSt. The viscosity index was 140. The weight average molecular weight was 1,025.

Example 8

100 g of 1-octene was added to a 250 mL flask filled with nitrogen. Heating was performed constantly at 120° C. for 30 minutes. 35 mg of trimethylammonium tetrakis(pentafluorophenyl)borate, 137 mg of tri-n-hexylaluminum and 2 μmol of dimethylsilylbisindenylzirconium dichloride were added successively. After the reaction was performed for 2 h, a small amount of isopropanol was added to terminate the reaction. After the temperature dropped to room temperature, the mixture was filtered and distilled under reduced pressure to obtain 80.26 g of a product with a yield of 80%. The 100° C. kinematic viscosity was 146.2 cSt. The viscosity index was 210. The weight average molecular weight was 6,991.

Example 9

100 g of 1-octene was added to a 250 mL flask filled with nitrogen. Heating was performed constantly at 20° C. for 30 minutes. 31 mg of trimethylammonium tetrakis(pentafluorophenyl)borate, 137 mg of tri-n-hexylaluminum and 2 μmol of diphenylsilylbis(4,7-dimethylindenyl)zirconium dichloride were added successively. After the reaction was performed for 10 h, a small amount of isopropanol was added to terminate the reaction. After the temperature dropped to room temperature, the mixture was filtered and distilled under reduced pressure to obtain 95.44 g of a product with a yield of 95%. The 100° C. kinematic viscosity was 104.5 cSt. The viscosity index was 237. The weight average molecular weight was 5,543.

Example 10

100 g of 1-octene was added to a 250 mL flask filled with nitrogen. Heating was performed constantly at 110° C. for 30 minutes. 29 mg of dibutylanilinium tetrakis(pentafluorophenyl)borate, 74 mg of tri-n-propylaluminum and 4 μmol of ethylenebisindenylzirconium dichloride were added successively. After the reaction was performed for 1 h, a small amount of isopropanol was added to terminate the reaction. After the temperature dropped to room temperature, the mixture was filtered and distilled under reduced pressure to obtain 96.42 g of a product with a yield of 96%. The 100° C. kinematic viscosity was 95.7 cSt. The viscosity index was 228. The weight average molecular weight was 5,238.

Example 11

100 g of 1-octene was added to a 250 mL flask filled with nitrogen. Heating was performed constantly at 120° C. for 30 minutes. 33 mg of dimethylanilinium tetrakis(pentafluorophenyl)borate, 74 mg of triisobutylaluminum and 4 μmol of ethylenebisindenylzirconium dichloride were added successively. After the reaction was performed for 1 h, a small amount of isopropanol was added to terminate the reaction. After the temperature dropped to room temperature, the mixture was filtered and distilled under reduced pressure to obtain 92.57 g of a product with a yield of 92%. The 100° C. kinematic viscosity 1 was 213.7 cSt. The viscosity index was 274. The weight average molecular weight was 9,335.

Example 12

100 g of 1-octene was added to a 250 mL flask filled with nitrogen. Heating was performed constantly at 120° C. for 30 minutes. 49 mg of diethylanilinium tetrakis(pentafluorophenyl)borate, 126 mg of tri-n-butylaluminum and 4 μmol of dimethylsilylbis(2-methyl-3-butylcyclopentadienyl)zirconium dichloride were added successively. After the reaction was performed for 1 h, a small amount of isopropanol was added to terminate the reaction. After the temperature dropped to room temperature, the mixture was filtered and distilled under reduced pressure to obtain 70.45 g of a product with a yield of 70%. The 100° C. kinematic viscosity was 320.8 cSt. The viscosity index was 276. The weight average molecular weight was 13,053.

Example 13

100 g of 1-decene was added to a 250 mL flask filled with nitrogen. Heating was performed constantly at 80° C. for 30 minutes. 37 mg of triethylammonium tetrakis(pentafluorophenyl)borate, 43 mg of trimethylaluminum and 2 μmol of ethylenebisindenylzirconium dichloride were added successively. After the reaction was performed for 3 h, a small amount of isopropanol was added to terminate the reaction. After the temperature dropped to room temperature, the mixture was filtered and distilled under reduced pressure to obtain 53.68 g of a product with a yield of 53%. The 100° C. kinematic viscosity was 18 cSt. The viscosity index was 190. The weight average molecular weight was 2,540.

Example 14

100 g of 1-decene was added to a 250 mL flask filled with nitrogen. Heating was performed constantly at 120° C. for 30 minutes. 41 mg of dimethylanilinium tetrakis(pentafluorophenyl)borate, 38 mg of trimethylaluminum and 3 μmol of dimethylsilylbiscyclopentadienylzirconium dichloride were added successively. After the reaction was performed for 1 h, a small amount of isopropanol was added to terminate the reaction. After the temperature dropped to room temperature, the mixture was filtered and distilled under reduced pressure to obtain 87.92 g of a product with a yield of 88%. The 100° C. kinematic viscosity was 35.5 cSt. The viscosity index was 200. The weight average molecular weight was 3,148.

Example 15

100 g of 1-decene was added to a 250 mL flask filled with nitrogen. Heating was performed constantly at 120° C. for 30 minutes. 45 mg of dimethylanilinium tetrakis(pentafluorophenyl)borate, 52 mg of triethylaluminum and 4 µmol of dimethylsilylbiscyclopentadienylzirconium dichloride were added successively. After the reaction was performed for 1 h, a small amount of isopropanol was added to terminate the reaction. After the temperature dropped to room temperature, the mixture was filtered and distilled under reduced pressure to obtain 93.02 g of a product with a yield of 93%. The 100° C. kinematic viscosity was 161 cSt. The viscosity index was 251. The weight average molecular weight was 7,505.

Example 16

100 g of 1-decene was added to a 250 mL flask filled with nitrogen. Heating was performed constantly at 60° C. for 30 minutes. 45 mg of dimethylanilinium tetrakis(pentafluorophenyl)borate, 68 mg of triethylaluminum and 6 µmol of dimethylsilylbiscyclopentadienylzirconium dichloride were added successively. After the reaction was performed for 3 h, a small amount of isopropanol was added to terminate the reaction. After the temperature dropped to room temperature, the mixture was filtered and distilled under reduced pressure to obtain 48.65 g of a product with a yield of 48%. The 100° C. kinematic viscosity was 387.5 cSt. The viscosity index was 216. The weight average molecular weight was 15,369.

Example 17

100 g of 1-decene was added to a 250 mL flask filled with nitrogen. Heating was performed constantly at 120° C. for 30 minutes. 15 mg of dimethylanilinium tetrakis(pentafluorophenyl)borate, 80 mg of triisopropylaluminum and 3 µmol of diethylmethylenecyclopentadienyl(3,5-dimethylphenylindenyl)zirconium dichloride were added successively. After the reaction was performed for 1 h, a small amount of isopropanol was added to terminate the reaction. After the temperature dropped to room temperature, the mixture was filtered and distilled under reduced pressure to obtain 94.85 g of a product with a yield of 95%. The 100° C. kinematic viscosity was 128 cSt. The viscosity index was 329. The weight average molecular weight was 6,359.

Example 18

100 g of 1-dodecene was added to a 250 mL flask filled with nitrogen. Heating was performed constantly at 200° C. for 30 minutes. 45 mg of diethylanilinium tetrakis(pentafluorophenyl)borate, 50 mg of triisobutylaluminum and 3 µmol of diethylmethylenecyclopentadienyl(3,5-dimethylphenylindenyl)hafnium dichloride were added successively. After the reaction was performed for 1 h, a small amount of isopropanol was added to terminate the reaction. After the temperature dropped to room temperature, the mixture was filtered and distilled under reduced pressure to obtain 93.66 g of a product with a yield of 93%. The 100° C. kinematic viscosity was 147 cSt. The viscosity index was 185. The weight average molecular weight was 7,019.

Example 19

100 g of 1-decene was added to a 250 mL flask filled with nitrogen. Heating was performed constantly at 140° C. for 30 minutes. 61 mg of dibutylanilinium tetrakis(pentafluorophenyl)borate, 50 mg of triethylaluminum and 3 µmol of dimethylsilylbisindenylzirconium dichloride were added successively. After the reaction was performed for 2 h, a small amount of isopropanol was added to terminate the reaction. After the temperature dropped to room temperature, the mixture was filtered and distilled under reduced pressure to obtain 88.27 g of a product with a yield of 88%. The 100° C. kinematic viscosity was 236 cSt. The viscosity index was 302. The weight average molecular weight was 10,109.

Example 20

100 g of 1-decene was added to a 250 mL flask filled with nitrogen. Heating was performed constantly at 120° C. for 30 minutes. 22 mg of trimethylammonium tetrakis(pentafluorophenyl)borate, 103 mg of tri-n-propylaluminum and 2 µmol of dimethylsilylbis(2-methylcyclopentadienyl)zirconium dichloride were added successively. After the reaction was performed for 1 h, a small amount of isopropanol was added to terminate the reaction. After the temperature dropped to room temperature, the mixture was filtered and distilled under reduced pressure to obtain 96.74 g of a product with a yield of 96%. The 100° C. kinematic viscosity was 197 cSt. The viscosity index was 278. The weight average molecular weight was 8,755.

Example 21

400 g of 1-decene was added to a 1,000 mL flask filled with nitrogen. Heating was performed constantly at 120° C. for 30 minutes. 88 mg of trimethylammonium tetrakis (pentafluorophenyl)borate, 1.2 mg of tri-n-propylaluminum and 8 µmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 326 g of a product with a yield of 81.5%. The 100° C. kinematic viscosity was 1,135 cSt. The viscosity index was 317. The weight average molecular weight was 41,322.

Example 22

400 g of 1-decene was added to a 1,000 mL flask filled with nitrogen. Heating was performed constantly at 120° C. for 30 minutes. 88 mg of trimethylammonium tetrakis (pentafluorophenyl)borate, 1.25 g of tri-n-propylaluminum and 8 µmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 248 g of a product with a yield of 62%. The 100° C. kinematic viscosity was 6 cSt. The viscosity index was 141. The weight average molecular weight was 1,350.

Example 23

100 g of 1-decene was added to a 250 mL flask filled with nitrogen. Heating was performed constantly at 120° C. for 30 minutes. 0.16 mg of dimethylanilinium tetrakis(pentafluorophenyl)borate, 133 mg of tri-n-propylaluminum and 2 µmol of dimethylsilylbis(2-methylcyclopentadienyl)zirconium dichloride were added successively. After the reaction was performed for 1 h, a small amount of isopropanol was added to terminate the reaction. After the temperature dropped to room temperature, the mixture was filtered and distilled under reduced pressure to obtain 73.52 g of a product with a yield of 73%. The 100° C. kinematic viscosity was 69 cSt. The viscosity index was 166. The weight average molecular weight was 4,311.

Example 24

100 g of 1-decene was added to a 250 mL flask filled with nitrogen. Heating was performed constantly at 120° C. for 30 minutes. 160 mg of dimethylanilinium tetrakis(pentafluorophenyl)borate, 133 mg of tri-n-propylaluminum and 2 μmol of dimethylsilylbis(2-methylcyclopentadienyl)zirconium dichloride were added successively. After the reaction was performed for 1 h, a small amount of isopropanol was added to terminate the reaction. After the temperature dropped to room temperature, the mixture was filtered and distilled under reduced pressure to obtain 83.14 g of a product with a yield of 83%. The 100° C. kinematic viscosity was 1,127 cSt. The viscosity index was 316. The weight average molecular weight was 41,045.

Example 25

100 g of 1-decene was added to a 250 mL flask filled with nitrogen. Heating was performed constantly at 120° C. for 30 minutes. 293 mg of dimethylanilinium tetrakis(pentafluorophenyl)borate and 2 μmol of dimethylsilylbis(2-methylcyclopentadienyl)zirconium dichloride were added successively. After the reaction was performed for 1 h, a small amount of isopropanol was added to terminate the reaction. After the temperature dropped to room temperature, the mixture was filtered and distilled under reduced pressure to obtain 0 g of a product with a yield of 0%.

Example 26

100 g of 1-decene was added to a 250 mL flask filled with nitrogen. Heating was performed constantly at 120° C. for 30 minutes. 293 mg of tri-n-propylaluminum and 2 μmol of dimethylsilylbis(2-methylcyclopentadienyl)zirconium dichloride were added successively. After the reaction was performed for 1 h, a small amount of isopropanol was added to terminate the reaction. After the temperature dropped to room temperature, the mixture was filtered and distilled under reduced pressure to obtain 5 g of a product with a yield of 5%. The 100° C. kinematic viscosity was 12 cSt. The viscosity index was 165. The weight average molecular weight was 1,857.

Example 27

The difference from Example 24 only lies in that the dosage of dimethylsilylbis(2-methylcyclopentadienyl)zirconium dichloride was adjusted to 0.1 μmol. 42.57 g of a product was obtained with a yield of 42%. The 100° C. kinematic viscosity was 1,305 cSt. The viscosity index was 345. The weight average molecular weight was 48,605.

Example 28

The difference from Example 24 only lies in that the dosage of dimethylsilylbis(2-methylcyclopentadienyl)zirconium dichloride was adjusted to 10 μmol. 98 g of a product was obtained with a yield of 98%. The 100° C. kinematic viscosity was 92 cSt. The viscosity index was 213. The weight average molecular weight was 5,047.

Example 29

400 g of 1-decene was added to a 1,000 mL flask filled with nitrogen. Heating was performed constantly at 120° C. for 30 minutes. 88 mg of trimethylammonium tetrakis(pentafluorophenyl)borate, 0.6 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 296 g of a product with a yield of 74%. The 100° C. kinematic viscosity was 1,085 cSt. The viscosity index was 310. The weight average molecular weight was 40,685.

Example 30

400 g of 1-decene was added to a 1,000 mL flask filled with nitrogen. Heating was performed constantly at 120° C. for 30 minutes. 176 mg of trimethylammonium tetrakis(pentafluorophenyl)borate, 1.2 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 348 g of a product with a yield of 87%. The 100° C. kinematic viscosity was 1,055 cSt. The viscosity index was 310. The weight average molecular weight was 39,605.

Example 31

400 g of 1-decene was added to a 1,000 mL flask filled with nitrogen. Heating was performed constantly at 120° C. for 30 minutes. 88 mg of trimethylammonium tetrakis(pentafluorophenyl)borate, 0.3 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 220 g of a product with a yield of 55%. The 100° C. kinematic viscosity was 946 cSt. The viscosity index was 308. The weight average molecular weight was 34,681.

Example 32

400 g of 1-decene was added to a 1,000 mL flask filled with nitrogen. Heating was performed constantly at 120° C. for 30 minutes. 88 mg of trimethylammonium tetrakis(pentafluorophenyl)borate, 2.4 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 352 g of a product with a yield of 88%. The 100° C. kinematic viscosity was 1,186 cSt. The viscosity index was 317. The weight average molecular weight was 43,321.

Example 33

400 g of 1-decene was added to a 1,000 mL flask filled with nitrogen. Heating was performed constantly at 120° C.

for 30 minutes. 88 mg of trimethylammonium tetrakis (pentafluorophenyl)borate, 24 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 368 g of a product with a yield of 92%. The 100° C. kinematic viscosity was 1,257 cSt. The viscosity index was 330. The weight average molecular weight was 45,877.

Example 34

400 g of 1-decene was added to a 1,000 mL flask filled with nitrogen. Heating was performed constantly at 120° C. for 30 minutes. 88 mg of trimethylammonium tetrakis (pentafluorophenyl)borate, 48 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 384 g of a product with a yield of 96%. The 100° C. kinematic viscosity was 1,289 cSt. The viscosity index was 335. The weight average molecular weight was 46,029.

Example 35

400 g of 1-decene was added to a 1,000 mL flask filled with nitrogen. Heating was performed constantly at 120° C. for 30 minutes. 88 mg of trimethylammonium tetrakis (pentafluorophenyl)borate, 270 mg of tri-n-propylaluminum and 8 μmol of dimethylsilylbis(2-methylcyclopentadienyl) zirconium dichloride were added successively. After the reaction was performed for 1 h, a small amount of isopropanol was added to terminate the reaction. After the temperature dropped to room temperature, the mixture was filtered and distilled under reduced pressure to obtain 332 g of a product with a yield of 83%. The 100° C. kinematic viscosity was 1,302 cSt. The viscosity index was 345. The weight average molecular weight was 48,021.

Comparative Example 1

The difference from Example 1 only lies in that the dimethylsilylbis-n-propylcyclopentadienylzirconium dichloride in Example 1 was replaced with methoxymethylsilylbis-n-propylcyclopentadienylzirconium dichloride. 65 g of a product was finally obtained with a yield of 65%. The 100° C. kinematic viscosity was 111.8 cSt. The viscosity index was 195. The weight average molecular weight is 5,649.

Comparative Example 2

The difference from Example 1 only lies in that the dimethylsilylbis-n-propylcyclopentadienylzirconium dichloride in Example 1 was replaced with a compound represented by the following formula (1) in CN107663257A with a dosage of 2 μmol (the dosage is consistent with that in Example 1). 45 g of a product was finally obtained with a yield of 45%. The 100° C. kinematic viscosity was 92 cSt. The viscosity index was 164. The weight average molecular weight is 4,937.

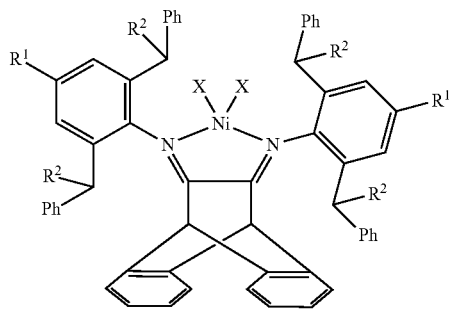

Formula (1)

In the formula (1), $R^1$ is H; $R^2$ is Ph; and X=Br.

Comparative Example 3

The difference from Example 1 only lies in that the trimethylaluminum in Example 1 was replaced with 32.2 mg of methylaluminoxane powder, which was obtained by vacuuming a commercially available methylaluminoxane toluene solution. 51 g of a product was finally obtained with a yield of 51%. The 100° C. kinematic viscosity was 80 cSt. The viscosity index was 190. The weight average molecular weight was 4,605.

Comparative Example 4

The difference from Example 1 only lies in that the dimethylanilinium tetrakis(pentafluorophenyl)borate in Example 1 was replaced with 20.4 mg of trispentafluorophenylboron. 22 g of a product was finally obtained with a yield of 22%. The 100° C. kinematic viscosity was 125 cSt. The viscosity index was 238. The weight average molecular weight was 6,125.

Comparative Example 5

The difference from Example 1 only lies in that no activator was used, and in other words, no dimethylanilinium tetrakis(pentafluorophenyl)borate and trimethylaluminum were used. 0 g of a product was finally obtained with a yield of 0%.

In order to facilitate comparison and analysis, the data in the above examples and comparative examples are summarized in the following tables 1-3.

TABLE 1

| Item | Polymerized monomer/dosage (g) | Metallocene compound/dosage (μmol) | Activator 1/dosage (mg) | Activator 2/dosage (mg) | Yield (%) | 100° C. kinematic viscosity (cSt) | Viscosity index | Weight average molecular weight |
|---|---|---|---|---|---|---|---|---|
| Example 1 | 1-hexene/100 | A1/2 | B1/32 | C1/40 | 70 | 120.6 | 237 | 6,102 |
| Example 2 | 1-hexene/100 | A2/3 | B1/32 | C1/40 | 75 | 111.8 | 220 | 5,797 |
| Example 3 | 1-octene/100 | A1/3 | B1/32 | C1/40 | 95 | 108.9 | 238 | 5,696 |

TABLE 1-continued

| Item | Polymerized monomer/dosage (g) | Metallocene compound/dosage (μmol) | Activator 1/dosage (mg) | Activator 2/dosage (mg) | Yield (%) | 100° C. kinematic viscosity (cSt) | Viscosity index | Weight average molecular weight |
|---|---|---|---|---|---|---|---|---|
| Example 4 | 1-octene/100 | A2/3 | B1/32 | C1/40 | 96 | 100.2 | 230 | 5,394 |
| Example 5 | 1-octene/100 | A1/3 | B1/32 | C2/55 | 94 | 101.7 | 229 | 5,446 |
| Example 6 | 1-octene/100 | A1/3 | B2/55 | C1/40 + C3/71 | 92 | 23.2 | 203 | 2,721 |
| Example 7 | 1-octene/100 | A3/2 | B3/35 | C4/102 | 81 | 5 | 140 | 1,025 |
| Example 8 | 1-octene/100 | A3/2 | B3/35 | C5/137 | 80 | 146.2 | 210 | 6,991 |
| Example 9 | 1- octene/100 | A4/2 | B3/31 | C5/137 | 95 | 104.5 | 237 | 5,543 |
| Example 10 | 1-octene/100 | A5/4 | B2/29 | C4/74 | 96 | 95.7 | 228 | 5,238 |
| Example 11 | 1-octene/100 | A5/4 | B1/33 | C6/74 | 92 | 213.7 | 274 | 9,335 |
| Example 12 | 1-octene/100 | A6/4 | B4/49 | C7/126 | 70 | 320.8 | 276 | 13,053 |
| Example 13 | 1-decene/100 | A5/2 | B5/37 | C1/43 | 53 | 18 | 190 | 2,540 |
| Example 14 | 1-decene/100 | A7/2 | B1/41 | C1/38 | 88 | 35.5 | 200 | 3,148 |
| Example 15 | 1-decene/100 | A7/4 | B1/45 | C2/52 | 93 | 161 | 251 | 7,505 |
| Example 16 | 1-decene/100 | A7/6 | B1/45 | C2/68 | 48 | 387.5 | 216 | 15,369 |
| Example 17 | 1-decene/100 | A8/3 | B1/15 | C3/80 | 95 | 128 | 329 | 6,359 |

TABLE 2

| Item | Polymerized monomer/dosage (g) | Metallocene compound/dosage (μmol) | Activator 1/dosage (mg) | Activator 2/dosage (mg) | Yield (%) | 100° C. kinematic viscosity (cSt) | Viscosity index | Weight average molecular weight |
|---|---|---|---|---|---|---|---|---|
| Example 18 | 1-dodecene/100 | A8/3 | B4/45 | C6/50 | 93 | 147 | 185 | 7,019 |
| Example 19 | 1-decene/100 | A9/3 | B2/61 | C2/50 | 88 | 236 | 302 | 10,109 |
| Example 20 | 1-decene/100 | A10/2 | B3/22 | C4/103 | 96 | 197 | 278 | 8,755 |
| Example 21 | 1-decene/400 | A10/8 | B3/88 | C4/1.2 | 81.5 | 1135 | 317 | 41,322 |
| Example 22 | 1-decene/400 | A10/8 | B3/88 | C4/1250 | 62 | 6 | 141 | 1,350 |
| Example 23 | 1-decene/100 | A10/2 | B1/0.16 | C4/133 | 73 | 69 | 166 | 4,311 |
| Example 24 | 1-decene/100 | A10/2 | B1/160 | C4/133 | 83 | 1127 | 316 | 41,045 |
| Example 25 | 1-decene/100 | A10/2 | B1/293 | — | 0 | — | — | — |
| Example 26 | 1-decene/100 | A10/2 | — | C4/293 | 5 | 12 | 165 | 1,857 |
| Example 27 | 1-decene/100 | A10/0.1 | B1/160 | C4/133 | 42 | 1305 | 345 | 48,605 |
| Example 28 | 1-decene/100 | A10/10 | B1/160 | C4/133 | 98 | 92 | 213 | 5,047 |
| Example 29 | 1-decene/400 | A10/8 | B3/88 | C4/0.6 | 74 | 1085 | 310 | 40,685 |
| Example 30 | 1-decene/400 | A10/8 | B3/176 | C4/1.2 | 87 | 1055 | 310 | 39,605 |
| Example 31 | 1-decene/400 | A10/8 | B3/88 | C4/0.3 | 55 | 946 | 308 | 34,681 |
| Example 32 | 1-decene/400 | A10/8 | B3/88 | C4/2.4 | 88 | 1186 | 317 | 43,321 |
| Example 33 | 1-decene/400 | A10/8 | B3/88 | C4/24 | 92 | 1257 | 330 | 45,877 |

TABLE 3

| Item | Polymerized monomer/dosage (g) | Metallocene compound/dosage (μmol) | Activator 1/dosage (mg) | Activator 2/dosage (mg) | Yield (%) | 100° C. kinematic viscosity (cSt) | Viscosity index | Weight average molecular weight |
|---|---|---|---|---|---|---|---|---|
| Example 34 | 1-decene/400 | A10/8 | B3/88 | C4/48 | 96 | 1289 | 335 | 46,029 |
| Example 35 | 1-decene/400 | A10/8 | B3/88 | C4/270 | 83 | 1302 | 345 | 48,021 |
| Comparative Example 1 | 1-hexene/100 | D1/2 | B1/32 | C1/40 | 65 | 111.8 | 195 | 5,649 |
| Comparative Example 2 | 1-hexene/100 | D2/2 | B1/32 | C1/40 | 45 | 92 | 164 | 4,937 |
| Comparative Example 3 | 1-hexene/100 | A1/2 | B1/32 | E1/32.2 | 51 | 80 | 190 | 4,605 |
| Comparative Example 4 | 1-hexene/100 | A1/2 | F1/20.4 | C1/40 | 22 | 125 | 238 | 6,125 |
| Comparative Example 5 | 1-hexene/100 | A1/2 | — | — | — | — | — | — |

Note: In the tables 1-3
A1 represents dimethylsilylbis-n-propylcyclopentadienylzirconium dichloride; A2 represents dimethylsilylbis-n-propylcyclopentadienylhafnium dichloride; A3 represents dimethylsilylbisindenylzirconium dichloride; A4 represents diphenylsilylbis(4,7-dimethylindenyl)zirconium dichloride; A5 represents ethylenebisindenylzirconium dichloride; A6 represents dimethylsilylbis(2-methyl-3-butylcyclopentadienyl)zirconium dichloride; A7 represents dimethylsilylbis-cyclopentadienylzirconium dichloride; A8 represents diethylmethylenecyclopentadienyl(3,5-dimethylphenylindenyl)zirconium dichloride; A9 represents dimethylsilylbisindenylzirconium dichloride; A10 represents dimethylsilylbis(2-methylcyclopentadienyl)zirconium dichloride;
B1 represents dimethylanilinium tetrakis(pentafluorophenyl)borate; B2 represents dibutylanilinium tetrakis(pentafluorophenyl)borate; B3 represents trimethylammonium tetrakis(pentafluorophenyl)borate; B4 represents diethylanilinium tetrakis(pentafluorophenyl)borate; B5 represents triethylammonium tetrakis(pentafluorophenyl)borate;
C1 represents trimethylaluminum; C2 represents triethylaluminum; C3 represents triisopropylaluminum; C4 represents tri-n-propylaluminum; C5 represents tri-n-hexylaluminum; C6 represents triisobutylaluminum; C7 represents tri-n-butylaluminum;
D1 represents methoxymethylsilylbis-n-propylcyclopentadienylzirconium dichloride; D2 represents the main catalyst adopted in Comparative Example 2;
E1 represents methylaluminoxane;
F1 represents trispentafluorophenylboron; and
"--" represents no substance or no data.

The invention claimed is:

1. A method for preparing a poly-alpha-olefin comprising subjecting an α-olefin to a polymerization reaction in the presence of a metallocene catalyst to obtain the poly-alpha-olefin,
wherein the polymerization reaction is carried out in the absence of a solvent,
the metallocene catalyst is formed of, or is formed by interaction between, a metallocene compound and an activator, the metallocene compound having a structural formula of formula (I):

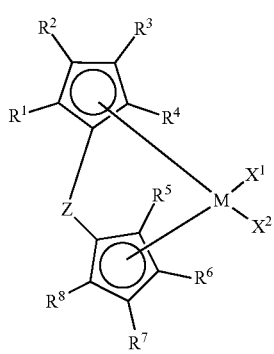

wherein M is titanium, zirconium, or hafnium;
$X^1$ and $X^2$ are each independently selected from a group consisting of halogens,
$R^1, R^2, R^3, R^4, R^5, R^6, R^7$, and $R^8$ are each independently selected from a group consisting of H, $C_1$-$C_{20}$ alkyl, $C_6$-$C_{20}$ aryl, $C_1$-$C_{20}$ substituted alkyl, $C_6$-$C_{20}$ substituted aryl, heteroatom substituted $C_1$-$C_{20}$ alkyl, and heteroatom substituted $C_6$-$C_{20}$ aryl,
Z is silicon that achieves valence saturation through a substituent, wherein the substituent is $C_1$-$C_{20}$ alkyl, $C_1$-$C_{20}$ substituted alkyl, or $C_6$-$C_{20}$ aryl, and
wherein the activator is an alkylaluminium and a borate, and a molar ratio of the alkylaluminium to the borate is (0.05-50):1,
wherein by calculating the alkylaluminium based on Al and the metallocene compound based on M, a molar ratio of the alkylaluminium to the metallocene compound is 0.1:1 to 1,000:1,
wherein the alkylaluminium is trimethylaluminum, triethylaluminum, triisopropylaluminum, tri-n-propylaluminum, triisobutylaluminum, tri-n-butylaluminum, triisoamylaluminum, tri-n-pentylaluminum, triisohexylaluminum, tri-n-hexylaluminum, triisoheptylaluminum, triisooctylaluminum, tri-n-octylaluminum, tri-n-heptylaluminum, triisononylaluminum, tri-n-nonylaluminum, triisodecylaluminum, or tri-n-decylaluminum,
wherein the borate is dimethylanilinium tetrakis(pentafluorophenyl) borate, diethylanilinium tetrakis(pentafluorophenyl) borate, dibutylanilinium tetrakis(pentafluorophenyl) borate, trimethylammonium tetrakis (pentafluorophenyl) borate, diethylammonium tetrakis (pentafluorophenyl) borate, or tributylammonium tetrakis(pentafluorophenyl) borate.

2. The method according to claim 1, wherein the molar ratio of the alkylaluminium to the borate is (0.05-20): 1.

3. The method according to claim 1, wherein the α-olefin is a $C_4$-$C_{20}$ α-olefin.

4. The method according to claim 1, wherein the polymerization reaction is carried out at a reaction temperature of 20° C. to 200° C.

5. The method according to claim 1, wherein by calculating the alkylaluminium based on Al and the metallocene compound based on M, a molar ratio of the alkylaluminium to the metallocene compound is 0.1:1 to 500:1.

6. The method according to claim 1, wherein a mass ratio of the metallocene compound to the α-olefin is ($10^{-6}$-$10^{-3}$): 1.

7. The method according to claim 1, wherein, in formula (I), $X^1$ and $X^2$ are each independently selected from a group consisting of chlorine, $C_1$-$C_4$ alkyl, $C_1$-$C_4$ substituted alkyl, and heteroatom substituted $C_1$-$C_4$ alkyl.

8. The method according to claim 1, wherein, in formula (I), $R^1, R^2, R^3, R^4, R^5, R^6, R^7$ and $R^8$ are each independently selected from a group consisting of H, $C_1$-$C_{10}$ alkyl, $C_6$-$C_{18}$ aryl, $C_1$-$C_{10}$ substituted alkyl, $C_6$-$C_{15}$ substituted aryl, heteroatom substituted $C_1$-$C_{10}$ alkyl, and heteroatom substituted $C_6$-$C_{15}$ aryl.

9. The method according to claim 1, wherein, in formula (I), Z is silicon that achieves valence saturation through a substituent.

10. A poly-alpha-olefin prepared by the method according to claim 1.

11. The poly-alpha-olefin according to claim 10, wherein the poly-alpha-olefin has a viscosity index of above 140.

12. The poly-alpha-olefin according to claim 10, wherein the poly-alpha-olefin has 100° C. kinematic viscosity of above 3 cSt.

13. The poly-alpha-olefin according to claim 1, wherein the poly-alpha-olefin has a weight average molecular weight of 200 to 50,000.

14. A lubricating oil, comprising the poly-alpha-olefin prepared by the method according to claim 1.

15. The method according to claim 1, wherein adjacent groups among $R^1$, $R^2$, $R^3$, $R^4$, $R^5$, $R^6$, $R^7$, and $R^8$ are bonded to each other to form cyclopentadienyl-aryl with a five-membered ring to which they are connected.

16. The method according to claim 3, wherein the α-olefin is selected from a group consisting of 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadene and 1-eicosene.

17. The method according to claim 3, wherein the α-olefin is selected from a group consisting of 1-butene, 1-pentene, 1-hexene, 1-heptene, 1-octene, 1-nonene, 1-decene, 1-undecene, 1-dodecene, 1-tridecene, and 1-tetradecene.

\* \* \* \* \*